US007908908B2

(12) United States Patent
Brown et al.

(10) Patent No.: US 7,908,908 B2
(45) Date of Patent: Mar. 22, 2011

(54) MATERIALS AND METHODS FOR IDENTIFYING BIOINTERACTIVE NANOSTRUCTURES AND/OR NANOPARTICLES

(75) Inventors: Scott C. Brown, Gainesville, FL (US); Brij M. Moudgil, Gainesville, FL (US); Yakov I. Rabinovich, Gainesville, FL (US); Veena B. Antony, Gainesville, FL (US); Mohammed A. Kamal, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 212 days.

(21) Appl. No.: 11/908,515

(22) PCT Filed: Mar. 23, 2006

(86) PCT No.: PCT/US2006/010828
§ 371 (c)(1),
(2), (4) Date: Sep. 13, 2007

(87) PCT Pub. No.: WO2006/102600
PCT Pub. Date: Sep. 28, 2006

(65) Prior Publication Data
US 2009/0000363 A1 Jan. 1, 2009

Related U.S. Application Data

(60) Provisional application No. 60/664,612, filed on Mar. 23, 2005.

(51) Int. Cl.
*G01B 5/28* (2006.01)
(52) U.S. Cl. ......................................................... 73/105
(58) Field of Classification Search .................... 73/105, 73/61.41; 116/275
See application file for complete search history.

(56) References Cited

U.S. PATENT DOCUMENTS

| 5,874,668 | A | 2/1999 | Xu et al. |
| 6,573,369 | B2 * | 6/2003 | Henderson et al. .......... 536/23.1 |
| 7,441,444 | B2 * | 10/2008 | Hoh ................................ 73/105 |

OTHER PUBLICATIONS

Characterisation of membrane surfaces: direct measurement of biological adhesion using an atomic force microscope Journal of Membrane Science, Elsevier Science, Amsterdam, NL vol. 154, No. 4 Mar. 17, 1999 pp. 205-212, XP004153961 Bowan et al.
Bowen W R et al. "Direct measurement of the force of adhesion of a single biological cell using an atomic force microscope." Colloids and Surfaces A: Physicochemical and Engineering Aspects Apr. 30, 1998 Vo. 136, No. 102 pp. 231-234.
Bowen et al. "Atomic force microscopy study of the adhesion of *Saccharomyces cerevisiae*" J. of Colloid and Interface Science, Academic Press, NY. NY US vol. 237, May 2001 pp. 54-61.
Benoit Martin et al.: "Discrete Interactions in cell adhesion measured by single-molecule force spectroscopy" Nature Cell Biology, vol. 2, No. 6, Jun. 2000 pp. 313-317.
Doneva T A. et al.: "Development and AFM study of porous scaffolds for wound healing applications" Spectroscopy 2004 Netherlands, vol. 18, No. 4, 2004, pp. 587-596.

* cited by examiner

*Primary Examiner* — Hezron Williams
*Assistant Examiner* — Rodney T Frank
(74) *Attorney, Agent, or Firm* — Timothy H. Van Dyke; Beusse Wolter Sanks Mora & Maire

(57) ABSTRACT

Disclosed herein are surface force microscope probes comprising living cells adhered thereto, as well as methods of making same. Also disclosed is a system for high throughput screening of nanostructures having biological relevance through use of surface force microscope probes comprising living cells. Further disclosed are methods of screening for biointeractive nanostructures.

5 Claims, 8 Drawing Sheets

Periodic Nanoscale Surface Features 1.5 nm RMS

Interaction between kidney epithelial cells retrieved from different organ sites with Calcium Oxalate Crystals in artificial urine.

LPCK Cells – No Adhesion

MDCK Cells – Adhesion (~0.5 nN)

→ Good Correlation with Kidney Stone Formation

MATERIALS AND METHODS FOR IDENTIFYING BIOINTERACTIVE NANOSTRUCTURES AND/OR NANOPARTICLES

RELATED APPLICATIONS

This application claims the benefit of U.S. Ser. No. 60/664,612 filed Mar. 23, 2005, under 35 USC §119(e) which is incorporated herein by reference.

The present invention was made with government support under grant number EEC-94-02989 from the National Science Foundation. Accordingly, the U.S. Government may have certain rights in the invention.

BACKGROUND

There is significant research and development interest in fabricating functional nano-bio interfaces for biomedical applications including advanced scaffolding[1,2], programmed differentiation[3], biocompatible device surfaces[4], sensors[5], etc. Progress in the discovery and isolation of uniquely-bioactive nanostructured surfaces has been severely limited due to the time and material intensive evaluation approaches currently practiced. Typical cell culture assays require days to weeks to perform and animal model studies can take weeks to years. Both normally require, at the very least, millimeter scale nanostructured materials, which can be a challenge to produce uniformly at those length scales and is often prohibitively expensive for screening applications. These barriers are further confounded by the shear plethora of possible nanoarchitectual configurations. The current approach to isolate potential structural candidates has been to look to nature and attempt to copy—this is tedious, time consuming, and often not cost effective. Moreover, limitations in current characterization technologies do not always allow for adequate interpretation and mimicking of nanoscale biological surfaces. With the exception of the enclosed invention, to date there are no methods for rapidly screening and isolating nanostructures that may exhibit unique properties in biological systems. Moreover, there exist no systematic methods for identifying structure-function correlations that can be used to forewarn of potential hazards as well as engineer 'smart' nanostructures for eliciting a specific bio response.

BRIEF DESCRIPTION OF DRAWINGS

FIG. 8a shows a top view of a body portion, FIG. 8b shows a top view of a lid portion, and FIG. 8c shows a top view of the assembled portions.

FIG. 9a shows a partial perspective view and partial side cross-sectional view of the embodiment and FIG. 9b shows the effect of micromanipulation.

DETAILED DESCRIPTION

Figure 1:
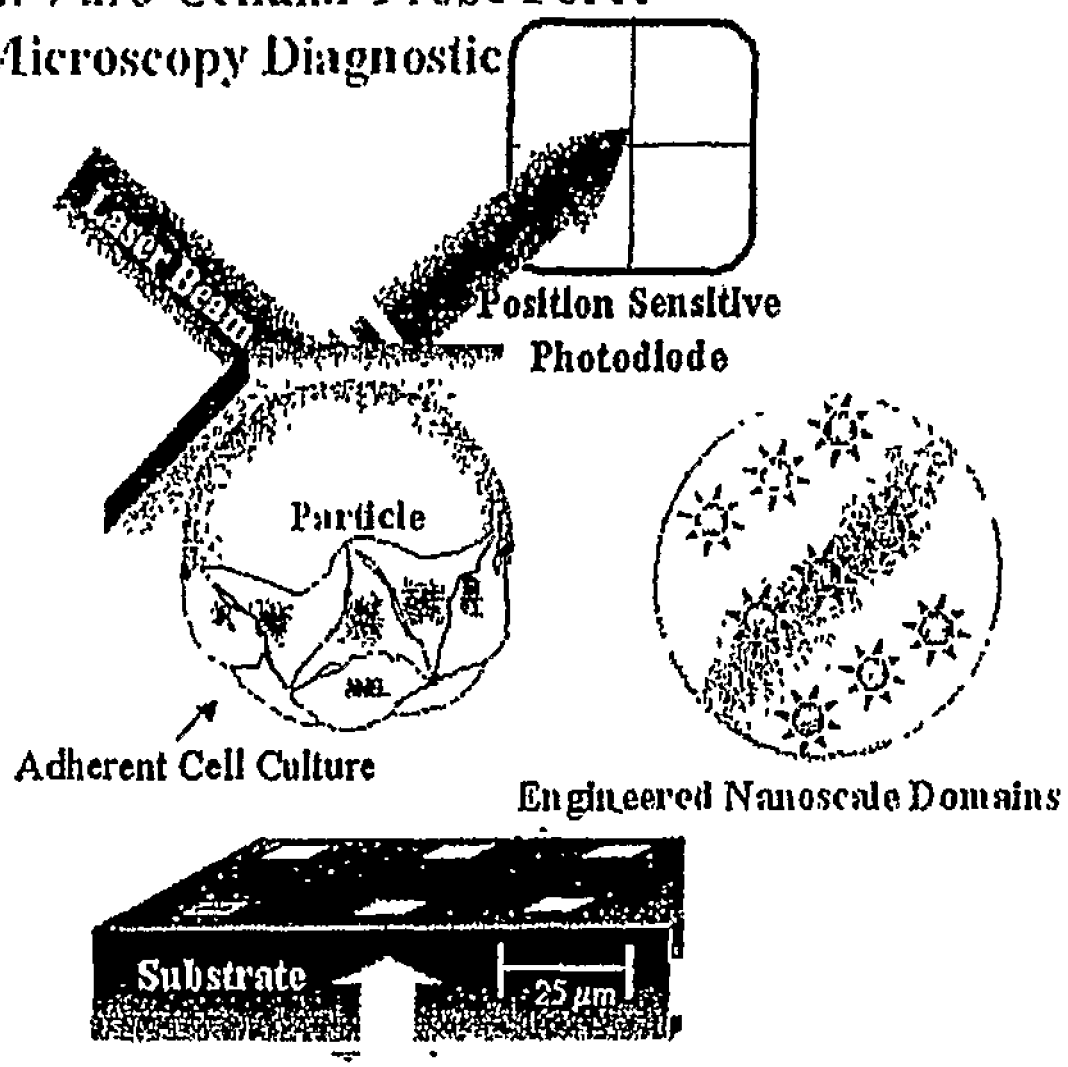
FIG. 1 is a schematic depicting a CPFM embodiment according to the teachings herein.

The subject invention was developed by the inventors discovery that general principles of surface (a.k.a., scanning) probe microscopy (SPM) technology may be adapted to develop novel probes as a screening tool for determining nanostructure bioactivity. According to a specific embodiment, the invention pertains to what will be called cellular probe force microscopy (CPFM). In one embodiment, CPFM involves the modification of a conventional liquid cell surface probe microscopy approach to employ a probe adapted to accommodate a living tissue culture. See FIG. 1 for an illustrative example. This may be achieved by attaching a fairly large particle (typically ~50 μm or larger, preferably ~100 μm or larger) to a commercial cantilever, subsequently seeding the particle with the cells of interest and allowing the cells to proliferate to confluency. This innovation provides the experimentalist with a large degree of freedom and opportunities not enabled by conventional in vitro SPM. By placing the cells of interest on the force sensor and not on the planar substratum, one is afforded the ability to scan cellular interactions with spatially resolved multiple domains of varying architecture (chemical and/or structural properties), thereby allowing assessment of multiple well-defined regions in a single experiment. SPM operation remains ultimately the same as typical liquid cell measurements. However, care must be taken not to delaminate or mechanically damage the cells cultured on the probe.

Those skilled in the art will appreciate that numerous surface adherent and semi-adherent cell types may be implemented for seeding cells onto a probe. Cell types include, but in no way are limited to epithelial, endothelial, fibroblasts, osteoblasts, progenitor cells, tumor cells, macrophages, neurons, stem cells etc. from a variety of living organisms (e.g., humans, rodents, primates, reptiles, and insects). Microorganisms may also be used for this embodiment.

Figure 2:
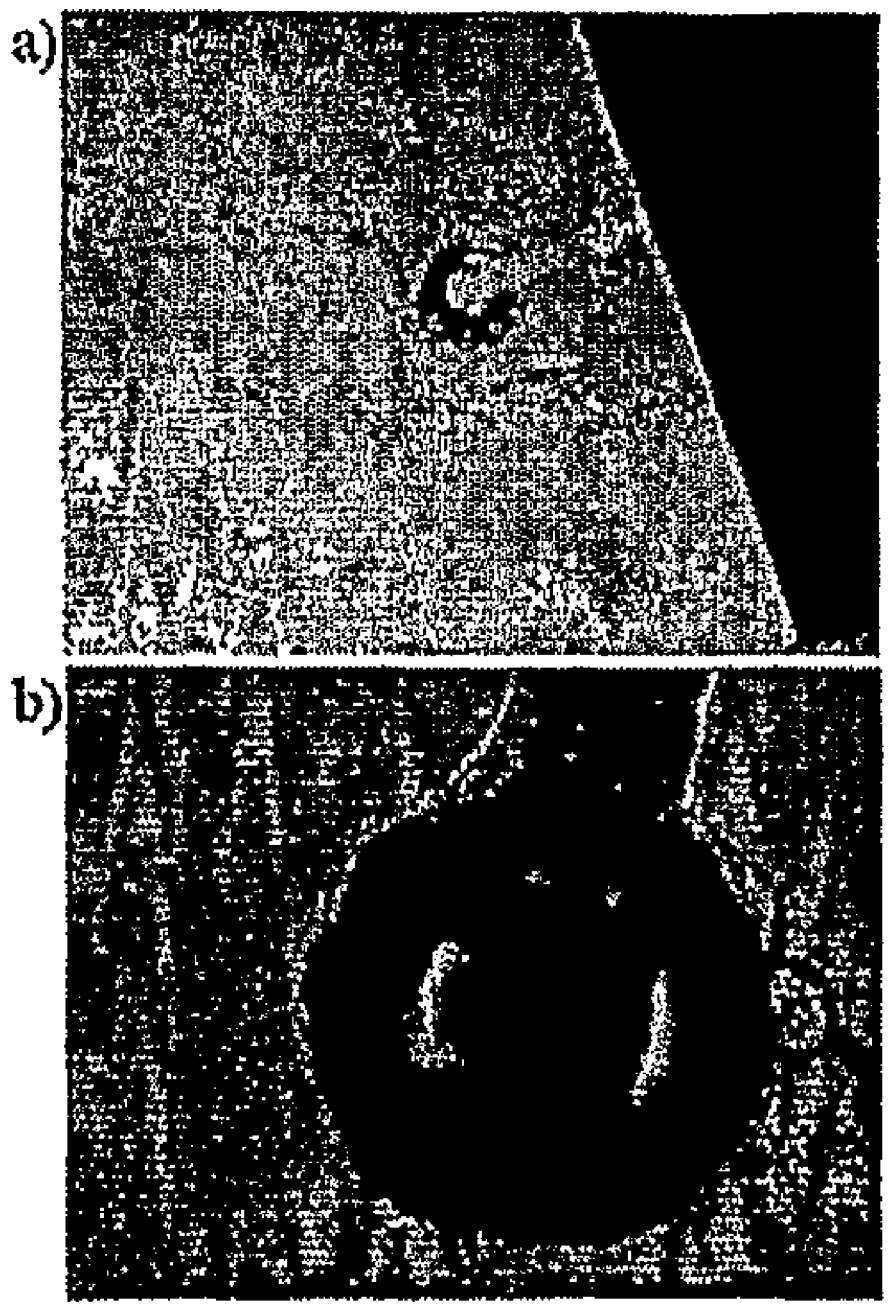
FIG. 2 shows optical micrographs of atomic force microscopy colloidal probe force sensors with attached mesothelial cells. a) full cantilever image b) zoomed image of colloidal probe with attached tissue culture

Thus, according to another embodiment, the subject invention pertains to CPFM probe that may be used in screening for biointeractive nanostructures and/or particles. See FIG. 2. In a specific embodiment, the inventors have created a living tissue culture stylus to be used as a read device for arrays of different nanostructure composition. The interpretation of adhesive and frictional interactions between the different patches will enable the interpretation of the potential biological activity of these structures with the probe cells under different physiological or artificial environments (liquid solutions etc.). Further, different components may be added to, or altered in the liquid cell, such as known bio-reagents, cell-signaling ligands, agonists, antagaonists, growth factors, ionic concentrations, etc and study their affect on the interaction between the cells on the probe and the nanostructure candidates. This technique may allow for data mining of tissue-nanostructure interactions in a means similar to that of the human genome project.

In yet another embodiment, the subject invention is directed to a method of screening for biointeractive nanostructures and/or nanoparticles. As used herein, the term biointeractive refers to those structures or particles that have an interactive relationship with cells or parts or components of cells. This interactive relationship may be, but not limited to, an attractive force or a repulsive force. The interactive relationship may also include a modulation of kinetics of such forces, e.g., the kinetics of adhesion events changes as a result of the interaction. This technique has additional promises in that it provides a method to measure interaction forces between engineered nanostructures and biologically-relevant confluent, differentiated tissue cultures. To date, no known interaction force measurements have been reported between engineered nanostructures and confluent, differentiated tissue cultures. The inventors believe that unique adhesive interactions exist between cells and specific nanoarchitectures under physiological conditions, and that these interactions can be used to predict unique longer-term biological endpoints. The ability to rapidly screen nanoarchitectual candidates for specific bioreactivity will help in understanding the impact of nanoarchitectures on cellular functions, and provide insights that may redefine how we build nano-bio interfaces. The method may include testing a microarray of different nanostructures disposed on a substrate, analyzing the interactive forces between the CPFM probe and the nanostructures, and identifying a nanostructure exhibiting an increased interactive force.

Nanostructures examined for biointeraction may be engineered utilizing a number of conventional techniques. Examples of such techniques are described in Chen and Pepin, *Electrophoresis*, 2001, 22:187-207; Marrian and Tennant, *J. Vac. Sci. Technol.*, 2003, 21:s207-215; and Gates et al., *Annu. Rev. Mater. Res.*, 2004 34:339-372, which are incorporated herein. E-beam lithography is specifically discussed below. Nanostructures engineered by this technique are generated according to a predetermined design. This avoids the work of having to later elucidate the characteristics of a structure randomly generated by other methods that is determined to be bioactive. Though, it should be pointed out that techniques that allow for predetermination of a structure or later determination can be implemented.

In another specific embodiment, method employs an SFM probe with attached living tissue culture. This probe is used to interrogate engineered nanostructures that are imprinted onto a planar substratum. For testing multiple nanostructures, small domains of nanostructures will be printed, etched, or otherwise applied to a single sustratum in optically, mechanically, or otherwise resolvable domains. In other words, domains (e.g. squares, patches, etc.) of nanostructured surfaces of intended test nanopatterns/nanostructures will be created such that they are distinguishable with regards to their preformed contents during and after the intended test.

According to another embodiment, the subject invention pertains to a method of screening for biointeractive nanostructures comprising providing a plurality of nanostructure candidates on a substrate; and interacting said nanostructure candidates with a surface force microscope probe comprising a cantilever unit that comprises a lever portion and a probe portion provided at a free end of said lever portion, said probe portion comprising one or more living cells adhered thereto; wherein a nanostructure candidate exhibiting adhesion. Interacting the probe and nanostructures may be noncontact or contact interaction. For noncontact interaction, the probe is brought in proximity with said nanostructure so as to allow for potential force(s) between them to be exerted. The identification of a biointeractive nanostructure may be assisted by comparison to a control structure or particle(s) or comparison among two or more nanostructures. Control nanostructures or particles consist of those that have been determined a priori by conventional cell culture/protein expression/gene expression techniques to not impose a significant change to the cells being used for interrogation, and/or represent baseline background values for adhesive interactions (i.e., background noise level). A nanostructure that deviates in adhesive characteristics from control nanostructures to said probe is identified as a biointeractive nanostructure.

Conventional approaches for determining biological interactions with nanoparticles and nanostructured materials, such as cell proliferation, viability, morphology and protein expression assays, are time intensive and offer little insight on how nanoarchitectual relationships may fundamentally influence interacting cells and tissues. The present approach will ultimately lead to a 'nano-bio' toolbox that may be used to forewarn of potential hazards as well as engineer 'smart' nanostructures for eliciting a specific bio response. Certain method embodiments described herein are based on the presumption that unique adhesive interactions exist between cells and specific nanoarchitectures under physiological conditions, and that these interactions can be used to predict unique longer-term biological endpoints.

In a specific embodiment, a nanostructure array is probed with multiple cell lines and potentially with multiple probes containing different cells in a single experiment. This enables a remarkably high throughput methodology for screening bioactive nanostructures.

Adhesive Interactions in Biological Environments.

Adhesive interactions in biological systems are normally driven by electrostatic, van der Waals and/or hydrophobic interactions—the same fundamental interactions that drive particle aggregation and deposition. However, in most biological cases a specific combination of these events are required which is further complicated by steric and stereochemical features that allow specific targeting (e.g. antigen-antibody) of molecular entities based upon peptide bond sequence and conformation. These interactions are typically reversible with selectivity and specificity driven by a balance between adhesive contacts that promote binding and thermal contributions that drive dissociation. However, when cells and/or biomolecules interact with large solid substratum the exchange process and the nature of adsorbed biomolecule can be different. Intermolecular contributions from particles size and morphology as well as surface site arrangements have been shown to cause denaturing of adsorbed biomolecules, and hystersis in adsorption/desorption profiles. These events have been utilized in biological systems for the immunological recognition of foreign materials, such that the potential hazards can be removed or encased by scar tissue. As feature size moves to the nanoscale, interactions appear to move into a meso-region between micro- and molecular interactions. In recent studies, selective adsorption of biomolecules onto nanomaterials have been reported[6], and in some cases adsorbed molecule activity has been maintained suggesting a reduction in denaturing with size[7].

Not intending to be bound by any particular theory, the inventors have postulated two primary routes through which adhesive interactions between foreign materials (especially nanoparticles/nanofunctionalized materials) and cells may have a larger biological consequence: active-participation and passive-interference. Active-participation implies that the material binds with cell surface receptors and/or modifies their spatial arrangement (causing localized aggregation, non-native associations, etc.) resulting in significant alterations in intracellular signaling (including induction of endocytosis/phagocytosis) or even cell membrane lysis. Whereas passive-interference suggests that the interaction of the material, itself, does not largely impact cellular function with the exception that its physical presence alters transmembrane transport processes, localized cytoskeletal function, localized dissolved species, and/or surface receptor availability.

The duration over which these events occur will undoubtably be critical in accessing the subsequent pathogenesis; however, without being bound to any particular theory, it is the inventors' belief that the existence and magnitude of an initial adhesive event upon contact will allude to the potential for altering processes within the interrogating cell culture. It is the establishment of these interactions that will dictate whether a particle will stay, leave, or be internalized by the cells of interest, and hence may predict subsequent events to come. The acquisition of this type of information under physiological conditions will provide information with regard to the target cells that exhibit attraction or repulsion toward a particular nanoscale material and perhaps provide information with respect to the mode of interaction.

Single molecule approaches have been developed which have aided in the fundamental understanding of biological ligand-receptor interactions—an important component to cell adhesion. In these methods, a biomolecule or engineered peptide sequence is directly attached to the apex of an AFM tip—usually with a mediating low interference spacer molecule, such as PEG (poly ethylene glycol), to minimize denaturing—and subsequently used to probe a test substrate comprising of a tissue culture, or receptor biomolecules, etc. Single molecule recognition force microscopy studies have allowed estimations of kinetic rates[8-11], energies, and structural parameters of the binding pocket[8-13].

Recently an imaging method for the mapping of antigenic sites on the surface was developed[14] by combining molecular recognition[8] with dynamic force microscopy (DFM)[13] With this methodology, topography and recognition images can be obtained at the same time and therefore receptor sites could be directly assigned to structures in the topography image[14]. However, while such work has merit, to the inventors' knowledge, the present invention is the first demonstration of a system capable of interrogating cell-nanostructure interactions utilizing the principles of SPM.

Advantages Over the State-of-the-Art.

A number of methods are available to measure cell adhesion to macroscopic surfaces (QCM-D, OWLS, SPR, mechanical detachment methods, cell morphology and spreading, etc). However, these methods measure the adhesion and subsequent reorganization and spreading of cell on substratum from a typically non-physiological detached state. It has been established that gene regulation and the expression of cell surface receptors is largely influenced by cell-cell and cell-substratum interactions; therefore it is quite plausible that initial adhesion measurements from cells in solutions to substratum may be misleading and different than that of confluent cells interacting to the same material. To the inventors' knowledge, CPFM is the only technique that allows for the direct measurement of the interaction of adherent confluent cell cultures to macroscopic substrates. Moreover, the CPFM approach may implement a smaller nanostructured area thereby minimizing cost and manufacturing time. The speed of analysis is further enhanced by imprinting nanostructured surfaces in a microarray format such that a single force sensor can analyze numerous well-defined types of nanostructures in a single experiment. Additionally, the presence of nanostructures on the substratum of optical and vibrational methods can lead to artifacts in measurement. Since the subject invention can measure adhesion directly, the subject invention does not suffer from this problem.

Measurements between single molecules and nanostructures can be both misleading and time consuming due to the number of potential binding molecules—which are often unknown. CFPM does not require a priori knowledge of the interacting molecular units. Moreover, most receptors, such as integrin cell adhesion receptors, require optimal cellular surroundings and organization within the plasma membrane in addition to association with lipids and accessory molecules to achieve their correct in vivo function and in vivo mechanical binding properties. Therefore, the subject invention enables the production of reliable data by investigating the binding properties of a given receptor within its physiological whole cell culture environment, as in the proposed methodology.

Example 1

Optimization of Living Tissue Culture Probes

The cellular probes are fabricated. Commercially available micron sized particles, in particular, microcarrier beads are screened for optimal cell culture performance. The growth rate, attachment and spreading of the primary culture is analyzed. The microcarrier bead that induces maximal proliferation and normal cell morphology is chosen. If a noticeable attachment of the cells occurs on the cantilever, the cantilevers are treated with a commercially available PEG-silane (Gelest Inc.) prior to particle attachment to prevent adhesion and potential optical interference with the reflected laser as used in conventional AFM. It should be noted that the elastic modulus of cells range from 1-100 kilopascals and therefore their presence on the cantilever should not affect the measured force; however, artifacts from anomalous scattering have been witnessed.

Cantilever stiffness is optimized to enhance reproducibility and sensitivity. This is necessary since the magnitude of interaction forces between the nanostructures and cells are unknown. Cells are known to have different adhesive properties to macroscopic surface based on their in vivo function. This property is often used to separate macrophages from fibroblasts, etc. Also, for a particular cell type, there may be several binding events (adhesive events), which may occur during interrogation, reflective of the high receptor concentration at the cell surface with varying number and type. Integrins may be present at millions of copies per cell, whereas growth factor receptors may be expressed at several orders of magnitudes less. The difference in the number of potential binding event clearly may have a large effect on the measured adhesive interactions. An iterative approach to cantilever spring constant choice is conducted to optimize reproducibility and required sensitivity for the CPFM system.

Example 2

Example of Cell Lines Employed by Probe

Primary cultures of human mesothelial cells (Clonetics Inc, San Diego, Calif.) were obtained from Cell Applications Inc. (San Diego, Calif.) and are cultured following the supplied guidelines in 75 cm$^2$ culture flasks. Cells between 3-8 passes and from one lot are used for these experiments. These cells have been selected due to prior culture expertise, as well as their similarity (maintained differentiation) to in vivo cells. The identity of the cells is confirmed as indicated in Table 1. Mesothelial cells are characterized by the presence of classic cobblestone morphology, absence of factor VIII antigen, and presence of cytokeratin.

TABLE 1

Characterization of pleural mesothelial cells
Pleural Mesothelial Cell Characteristics and Verification Criteria

| Cell Type | Factor VIII | Keratin | Vimentin | Morphology | Ricinus Communis Lectin |
|---|---|---|---|---|---|
| Mesothelial cell | − | + | + | Cobblestone microvilli | − |
| Fibroblasts | − | − | ± | Spindle shaped | − |
| Endothelial cells | + | − | + | Cobblestone no microvilli | − |
| Type 1 epithelial cells | ± | + | + | Cuboidal Few microvilli | + |

Those skilled in the art will appreciate that any number of characterized cells known in the art that may be implemented with the CPFM system. Routine experimentation may be implemented to optimize the conditions for implementing the cells on the probe.

Example 3

Nanostructure Array Fabrication & Interrogation

E-beam lithography is an example of a simple, cost and time efficient route for fabricating engineered nanostructures. A turn-key e-beam lithography unit such as those produced by Raith Gmbh (Dortmund, Germany) may be used and structures fabricated from the photoresist material may be used for interogation. Cell cultures on SU-8 photoresist materials, for example, have been studied for other biodevice applications and in vivo data suggests good biocompatibility and low native adhesion to macrophages[15]. Hence, some photoresist materials are adequate for initial studies. However, the same techniques may be employed to study interactions with etched/nanofabricated semiconductor oxide materials (silica, titania, silicon nitride, alumina, etc.), metalized surfaces (aluminum, copper, gold, platinum, etc.), coated or thin film surfaces (organic and inorganic films) and deposited particulate structures via microcontact printing (e.g. edge-transfer lithography). For the purposes of this example a fully automated Raith 150 ebeam lithography is used in conjunction with the widely used SU-8 photoresist material. Reactive ion etching may also be implemented to fabricate nanostructures in silica for additional experiments.

For this example, simple nanostructured designs will be tested first. To maximize the experimental time for interrogating nanostructured candidates a Dimension 3100 AFM (Veeco Inc.) with attached environmental chamber (37° C., 5% $CO_2$) and wafer sampling stage is be used. This particular AFM is advantageous, since the piezo is attached to the cantilever and not the planar substrate. This feature allow for one to probe a much larger area than otherwise. Each nanostructured patch will exist on a 50 by 50 micron SU-8 island separated by trenches 20 microns wide. A square grid containing 25 islands will be used during the initial experiments. The Dimension 3100's real-time optical microscope assisted step-motor driven stage will allow us to (1) see the defined microarray patches and (2) accurately probe them individually. The study begins by measuring interaction between imprinted nanolines and nanodots of approximately 30 nm width with variable spacings. Experimental variables are interactively adjusted with experimentation and measurements are made in culture media, both with and without serum. It should be noted that nanofiber-type arrangements have been reported to promote cell-adhesion and differentiation in the past. The probability distribution of an adhesive contact during force-volume measurement may be used to interpret the results as in single molecule methods. Additionally, a lateral force imaging may be conducted for reading the arrays.

1) The microarray strategy for nanostructure property data mining is very unique—current approaches to identify nanostructures with unique properties (biological, electronic, magnetic, etc.) typically rely on the fabrication of nanostructures either on multiple substrates (resulting in much longer analysis times) or over larger areas, which results in poor structure uniformity (resulting in characterization issues) or limited structural configurations that result in either prohibitively high costs or limited applicability to data mining. The approach outlined herein is highly applicable to data mining. It is also to the inventors knowledge the first systematic approach towards experiment driven nanomaterial-informatics.

2) The concept that adhesive cell signatures can be used to identify the existence of bioactive nanostructure is also unique. Current approaches to identifying bioactive nanostructure rely on in vitro or in vivo experimentation that requires days to years to perform. Certain method embodiments of the subject invention can be performed in a matter of seconds. This is a key feature that allows for an informatics approach to be implemented. An adhesive signature comprises both the time (frequency) and the nanoscale distance dependant force profiles between the probe and the surface. This type of information is not obtainable by any other method and to their knowledge; the inventors are the first to begin to investigate these features and how they relate to longer-term bioactivity.

Example 4

Correlation to Longer-Term In-Vitro Results

Structures that elicit a significant adhesive response, and randomly selected structures that do not are scaled up to 1.5 mm by 1.5 mm areas. Cells are cultured on these larger sections and accessed for changes in viability, proliferation and protein expression. Planar non-embossed substratum of the test material and a normal culture dish are used as controls.

Conventional techniques may be used to determine the longterm biological impact of nanostructure interaction. Alamar Blue assays will be used to monitor in situ proliferation. Cell counting utilizing trypan blue dye exclusion as well as flourescent live-dead kits may be implemented for determining cell viability on the surfaces (the later also for cell viability on the probe). Nano-HPLC electrospray MS/MS may be used to determine if a significant change in protein expression has occurred.

Example 5

Validation of Probe

Rectangular tipless cantilevers (MikroMasch) with a normal spring constant in the range of $K_N=5\pm0.5$ N/m—as determined by the frequency method—were used for this example. Cellular probes were fashioned via use of a micromanipulator and optical microscope by attaching a microcarrier bead to the end of a tipless cantilever with a small amount of a medical device epoxy adhesive (Loctite Hysol M-21HP). Once the glue had set, the cantilevers were immersed in 70% alcohol for three hours, dried and then autoclaved. Sterile probes were placed on the bottom of a culture dish with the microcarrier-side facing up and seeded with mesothelial cells at a concentration of 500,000 cells/ml to enhance the probability of cell attachment to the probe surface. The probes were incubated for eight hours at 37° C. after which probes with sufficient cell attachment (confirmed optically) were transferred to a new culture dish containing excess media and incubated until ~90% confluency. The normal forces and contact frictional interactions between two layers of pleural mesothelial cell, mesothelial cells and various substratum, were measured using this cellular probe force microscopy (CPFM).

Figure 3:
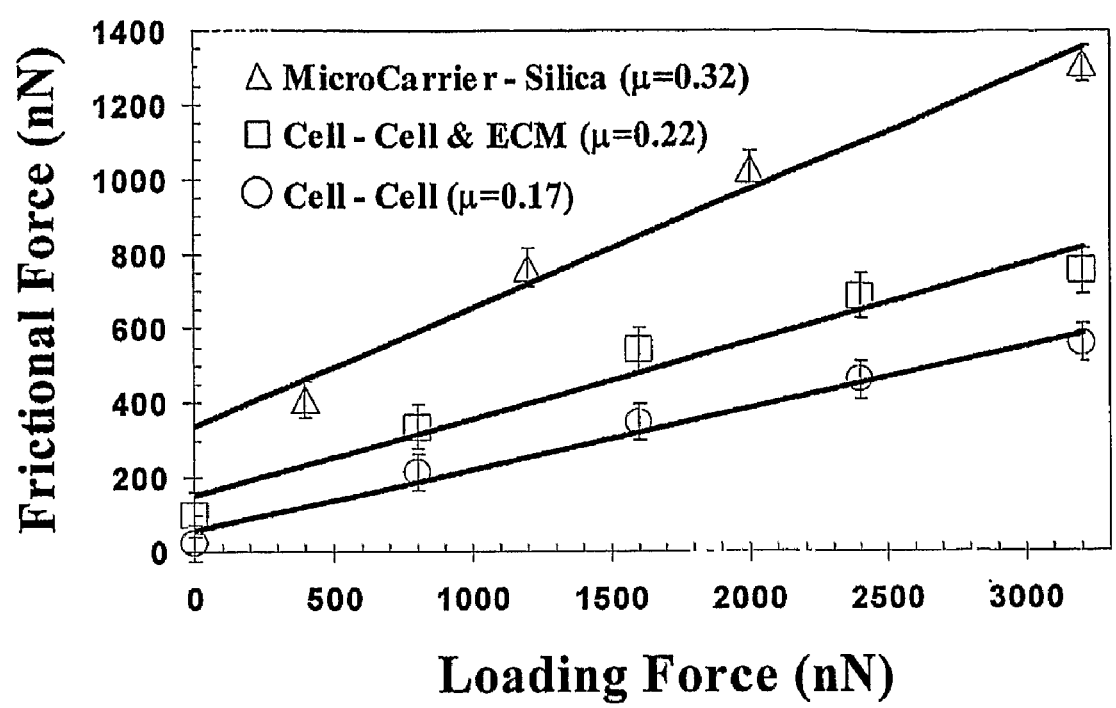
FIG. 3 is a graph showing AFM lateral force as measured between a clean 90 micron microcarrier bead and smooth silica surface (triangles), the same probe coated with a partially denuded pleural mesothelial cell layer (squares) interacting with a confluent layer of cells, and the same probe with a confluent coating of cells interacting with an opposing layer of cells, also confluent (diamonds). Measurements were made at 1 hertz over a lateral distance of 50 microns.
Figure 4:
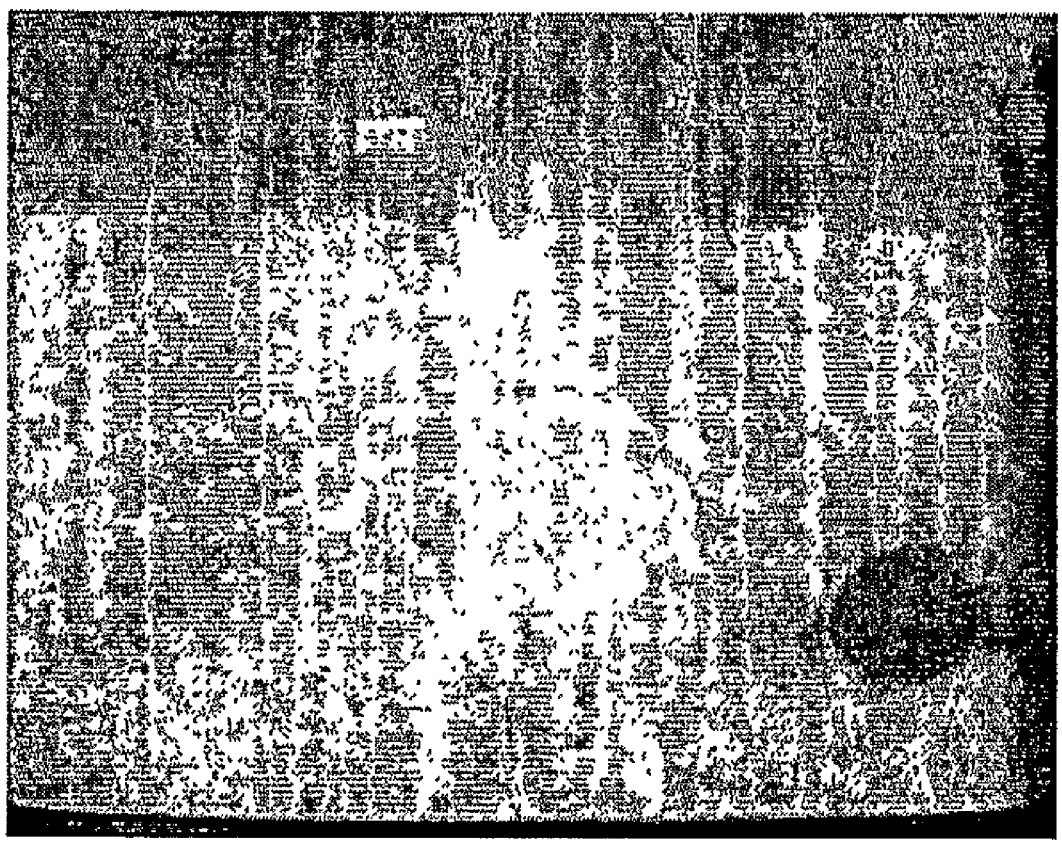
FIG. 4 is an optical micrograph (top view) illustrating delamination of mesothelial cells (center) after contact with a denuded mesothelial probe (bottom right). Delamination did not occur with either clean microcarrier or mesothelial cell-coated probe with an opposing PMC layer. The adhesive force measured during this interaction is represented in FIG. 5.

Since the integrity of the cells is questionable upon contact, frictional and normal interactions between two layers of basement membrane proteins as well as asymmetric cell membrane-basement protein interactions were investigated. As indicated in FIG. 3, the lateral interactions between two confluent mesothelial cell monolayers yielded a friction coefficient (μ) of approximately 0.17 N/m—illustrating significant interaction between contacting bare mesothelial monolayers. For comparison, the friction coefficient between the glass-coated microsphere surface and bare silica substrate was measured and found to be near 0.32 N/m, which is in good agreement with values reported for silica-silica friction in the literature. Attempts to directly measure the lateral interactions between a basement membrane and a monolayer of mesothelial cells were unsuccessful due to a strikingly large adhesion between the basement membrane and mesothelial cells. This adhesion force was large enough to cause cells to delaminate from the opposing substrate (FIG. 4). The resulting lateral forces measured were therefore a composite of the interactions between the mesothelial cells and ECM with an opposite confluent monolayer. The interpreted results are plotted in FIG. 5. Delamination was not seen in the case of cell-cell tribology under identical and slightly higher loading conditions.

Figure 5:
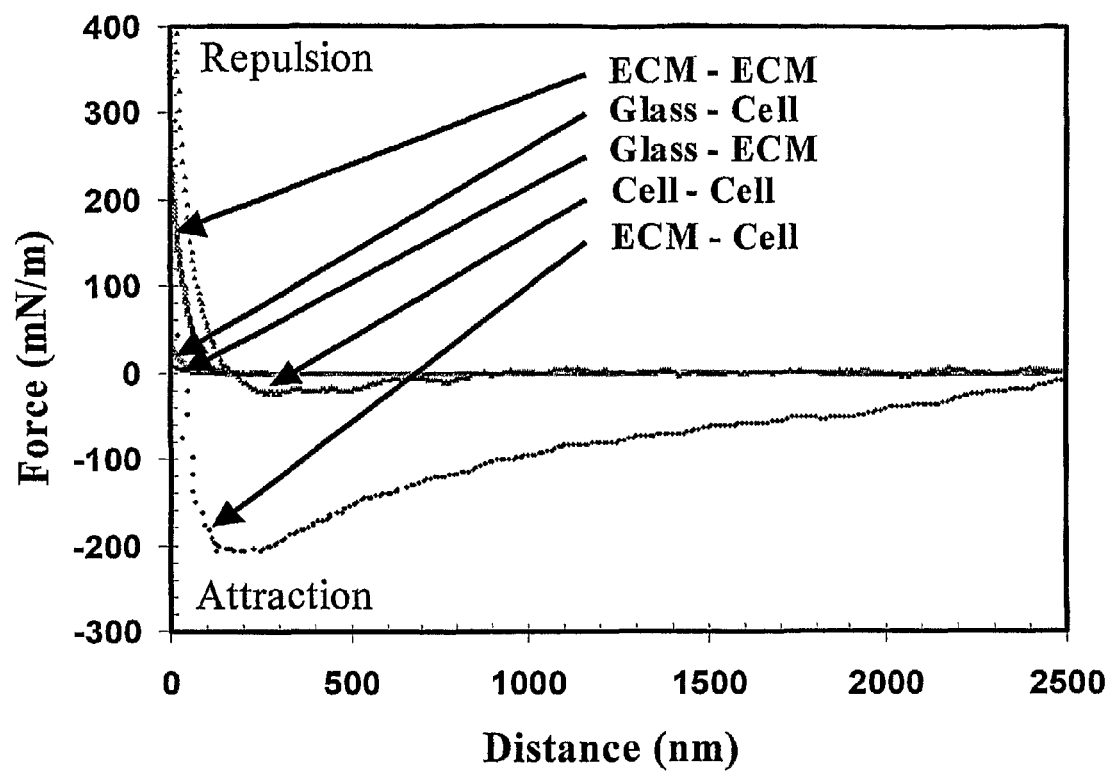
FIG. 5 is a graph showing pull-off forces as measure between PMC-PMC (red), denuded surface-denuded surface (green), clean microsphere-denuded surface (brown), clean microsphere-PMC, and denuded surface-PMC contact. A large adhesive force is observed in the case of denuded surface-PMC contact. It should be noted that the slight adhesion observed during cell-cell contact increased with approach velocity and hence appears to be attributed to viscous contributions from cell deformation.

To ensure that the adhesive interaction force was due to cellular interactions with components of the excreted basement membrane, several normal interaction force measurements were performed as indicated in FIG. 5. In all cases, no considerable intermolecular adhesion was noted except in the case of Cell-Cell and ECM-mesothelial cell contact. Under these circumstances, catherin and integrin-based binding are thought to occur. Hence, sensitivity of the method to cell-cell and cell-surface binding is demonstrated. The preliminary studies above, illustrate that the CPFM technique is sensitive enough to directly probe cell receptor-ligand binding.

Figure 10:
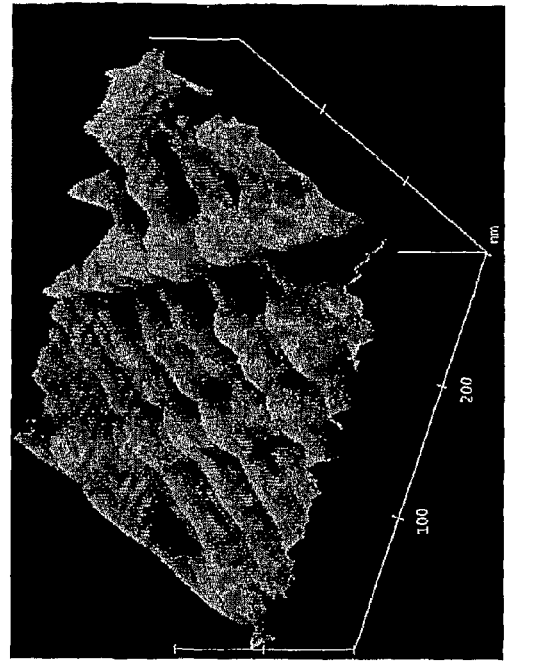
FIG. 10 graph showing interaction between kidney epithelial cells retrieved from different organ sites with Calcium Oxalate Crystals in artificial urine.
Figure 10:
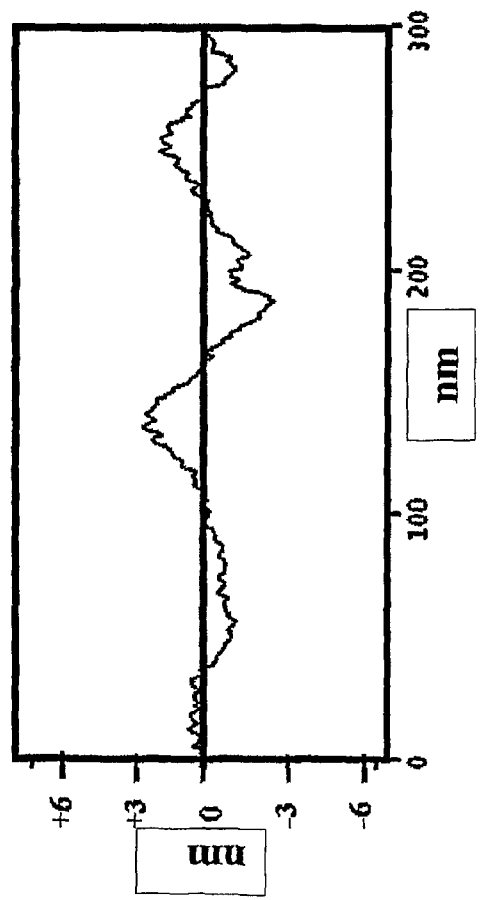

In related studies, surface force interactions between calcium oxalate colloidal probes and kidney epithelium cells have been investigated to delineate important mechanisms in the pathogenesis of kidney stone formation. Calcium oxalate is a primary constituent of kidney stones. Under artificial urine conditions—containing only ions—calcium oxalate crystals it has been shown that the oxalate crystals significantly bind to one type of kidney epithelial cell (MDCK), but not to another (LPCK). The adhesive interaction were 0.5+/−0.05 nN and less than 0.03 nN, respectively (See FIG. 10). These results correspond to observation that the areas from which the first cell was derived is known to have high kidney stone occurrence, whereas stones are not frequent where the LPCK epithelial cells were taken. In context to the examples above, it brings support to the hypothesis that differential adhesion between cells and artificially derived materials can predict subsequent and unique biological endpoints, which may have in vivo significance. Accordingly, in another embodiment, the subject invention pertains to identifying nanostructures having differential biointeractivity among two or more different cell types. This information will provide the ability to generate structures and surfaces having specificity to certain cell types.

Example 6

Biointeractive Nanostructure Database

In a further embodiment, the subject invention is directed to a compilation of data of measured interactive forces of certain nanostructures and particles. This compilation of information is typically provided in a computer readable database, that may also be accessed remotely via some communicative means such as the internet. As will be appreciated by one of skill in the art, embodiments of the present invention may be embodied as a device, method, or system comprising a processing module, and/or computer program product comprising at least one program code module. Accordingly, the present invention may take the form of an entirely hardware embodiment or an embodiment combining software and hardware aspects. Furthermore, the present invention may include a computer program product on a computer-usable storage medium having computer-usable program code means embodied in the medium. Any suitable computer readable medium may be utilized including hard disks, CD-ROMs, DVDs, optical storage devices, or magnetic storage devices.

The computer-usable or computer-readable medium may be or include, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM), a CD ROM, a DVD (digital video disk), or other electronic storage medium. Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Those skilled in the art should appreciate that the database of nanostructure information may be implemented over a network environment. That is, the remote user may be a client on a number of conventional network systems, including a local area network ("LAN"), a wide area network ("WAN"), or the Internet, as is known in the art (e.g., using Ethernet, IBM Token Ring, or the like). Typically, the remote user accesses the system via the internet.

Example 7

Other Embodiments

Based on the teachings herein, those skilled in the art will appreciate that CPFM system can be developed into stand-alone kits and instrumentation for monitoring cell-nanostructure interactions. Also, as biointeractive information of different nanostructures are elucidated, biomedical devices and applications utilizing characterized materials will be enabled.

Figure 6A:
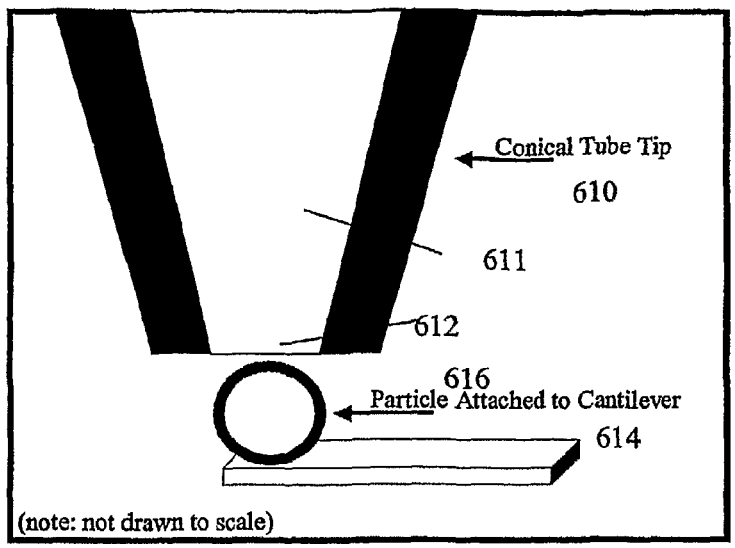
FIG. 6a-c shows a method of seeding a cantilever unit with living cells.
Figure 6B:
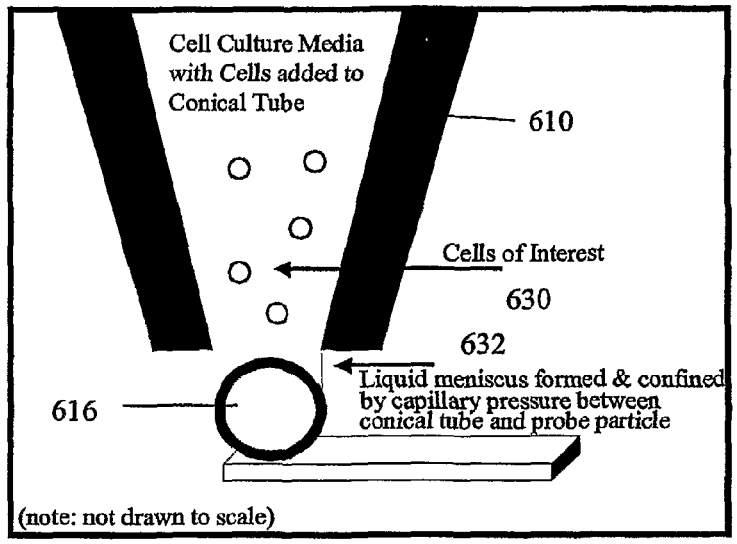
Figure 6C:
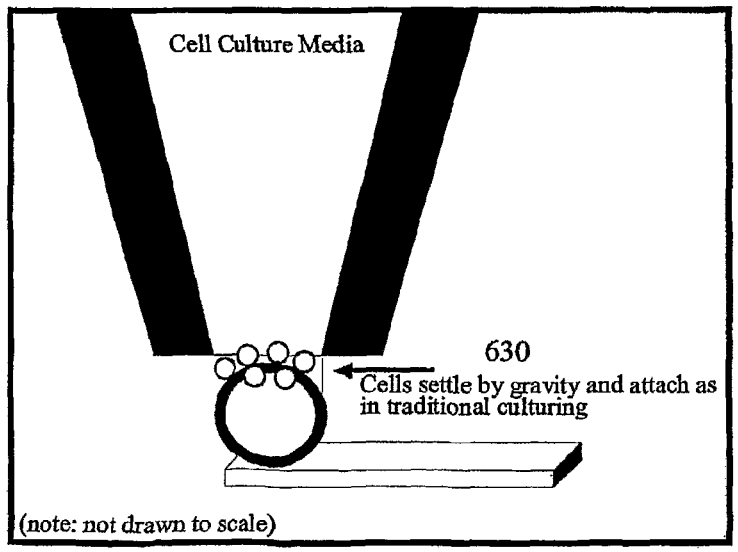

FIG. 6 shows one embodiment representing a method of seeding cell(s) onto a probe particle. FIG. 6a shows a conical tube 610 comprising a reservoir 611 into which a cell sample may be disposed (see FIG. 6b) and an outlet 612 that is positioned above a probe particle 616 attached to a cantilever 614. The conical tube could be substituted with some other reservoir comprising an outlet. The outlet 612 should be of a size so as to be able to delivery cells onto to the probe particle 616. FIG. 6b shows cells of interest 630 disposed within the reservoir 611 and which are delivered to the probe 616. The cells are in media that forms a meniscus between the conical tube 610 and probe particle 616. FIG. 6c shows that the cells of interest 630 settle onto the probe particle 616 by gravity.

Figure 7:
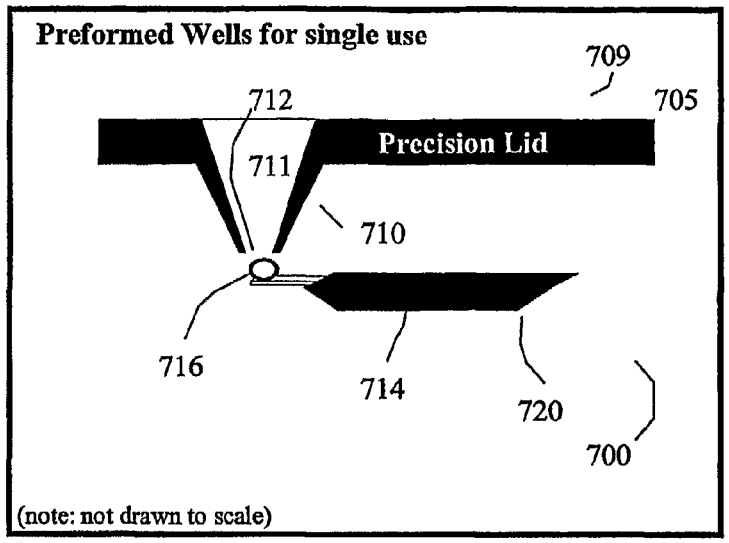
FIG. 7 shows a side cross section of an article of manufacture embodiment.

FIG. 7 shows a side view of an article of manufacture 700 that comprises an encasement 705 comprising a lid 709 and a body portion 720. Together the lid 709 and body portion encase a cantilever unit 714 comprising a probe particle 716 attached thereto. The lid 709 comprises a conical tube 710 portion. The tube 710 defines a reservoir 711 and an outlet 712. The cantilever 714 is placed within the space (or well) 722 defined by the encasement 705 such that a cell sample placed in the reservoir 711 may be delivered to the probe particle 716 via outlet 712. The article of manufacture may have a single well or multiple wells as further described for FIG. 8.

Figure 8:
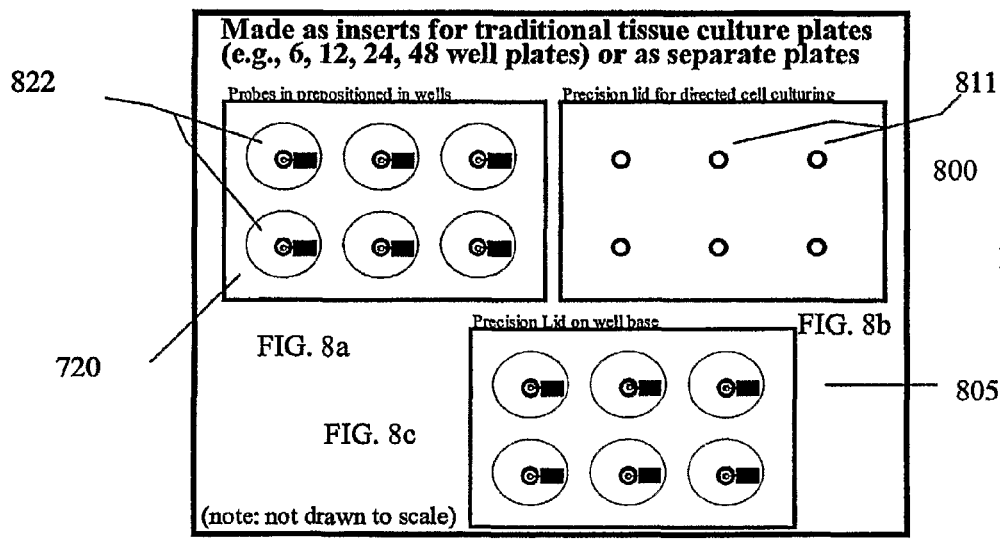
FIG. 8 shows a top view of an article of manufacture embodiment.

FIG. 8 shows a top view of another article of manufacture embodiment 800 that comprises a multitude of cantilevers 814. The embodiment 800 comprises a body portion 820 comprising a multitude of wells 822 defined therein into which the cantilevers 814 are disposed (see FIG. 8a). The embodiment also comprises a lid 809 having a multitude of reservoirs 811 defined therein having outlets that open into the body portion 820. The reservoirs may be configured into a conical tube form such as that shown in FIG. 7. FIG. 8c shows a top view of the encasement 805 formed by the assembled body 820 and lid 811 shown in FIGS. 8a and 8b, respectively.

Figure 9:
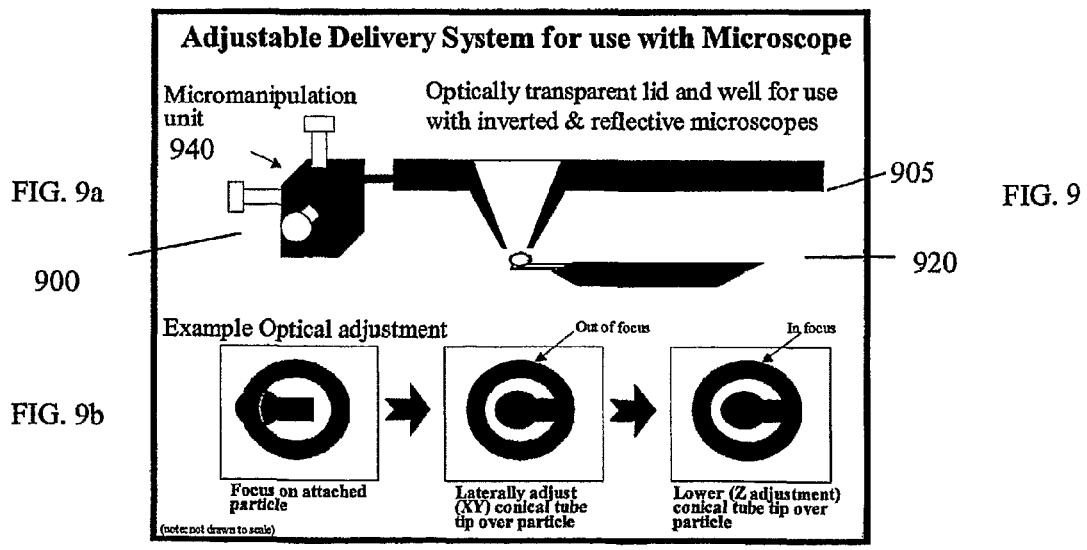
FIG. 9 shows a diagram of an micromanipulated article of manufacture embodiment.

FIG. 9 shows an alternative embodiment similar 900 to that shown in FIG. 7 except that the lid 909 is slidably engaged to the body portion 920. The lid 905 is associated with a micromanipulation unit 940 that allows for micromanipulation of the lid. FIGS. 9b-d show operation of the micromanipulation unit 940 to adjust the lid 905 to a target position.

1. RELEVANT REFERENCES

1. Min, B. M., Y. You, et al. (2004). "Formation of nanostructured poly(lactic-co-glycolic acid)/chitin matrix and its cellular response to normal human keratinocytes and fibroblasts." *Carbohydrate Polymers* 57 (3): 285-292.
2. Woehrle, G. H., M. G. Warner, et al. (2004). "Molecular-level control of feature separation in one-dimensional nanostructure assemblies formed by biomolecular nanolithography." *Langmuir* 20 (14): 5982-5988.
3. Silva, G. A., C. Czeisler, et al. (2004). "Selective differentiation of neural progenitor cells by high-epitope density nanofibers." *Science* 303 (5662): 1352-5.
4. Ronco, C., S. K. Bowry, et al. (2002). "Hemodialyzer: from macro-design to membrane nanostructure; the case of the FX-class of hemodialyzers." *Kidney Int Suppl* (80): 126-42.
5. Sotiropoulou, S. and N. A. Chaniotakis (2003). "Carbon nanotube array-based biosensor." *Analytical and Bioanalytical Chemistry* 375 (1): 103-105.
6. Woo, K. M., V. J. Chen, et al. (2003). "Nano-fibrous scaffolding architecture selectively enhances protein adsorption contributing to cell attachment." *Journal of Biomedical Materials Research Part A* 67A(2): 531-537.
7. Vertegel, A. A., R. W. Siegel, et al. (2004). "Silica nanoparticle size influences the structure and enzymatic activity of adsorbed lysozyme." *Langmuir* 20 (16): 6800-6807.
8. Hinterdorfer, P., W. Baumgartner, et al. (1996). "Detection and localization of individual antibody-antigen recognition events by atomic force microscopy." *Proceedings of the National Academy of Sciences of the United States of America* 93 (8): 3477-3481.
9. Hinterdorfer, P., A. Raab, et al. (1998). "Force spectroscopy of antibody-antigen recognition measured by scanning force microscopy." *Biophysical Journal* 74 (2): A186-A186.
10. Kienberger, F., A. Raab, et al. (2000). "Contact and mac-mode molecular recognition force microscopy (MRFM): Force spectroscopy of polyethylene glycol." *Biophysical Journal* 78 (1): 381a-381a.
11. Baumgartner, W., P. Hinterdorfer, et al. (2000). "Cadherin interaction probed by atomic force microscopy." *Proc Natl Acad Sci USA* 97 (8): 4005-10.
12. Willemsen, O. H., M. M. E. Snel, et al. (1998). "Simultaneous height and adhesion imaging of antibody-antigen interactions by atomic force microscopy." *Biophysical Journal* 75 (5): 2220-2228.
13. Han, W., S. M. Lindsay, et al. (1997). "Kinked DNA." *Nature* 386 (6625): 563.
14. Raab, A., W. Han, et al. (1999). "Antibody recognition imaging by force microscopy." *Nat Biotechnol* 17 (9): 901-5.
15. Voskerician, G., M. S. Shive, et al. (2003). "Biocompatibility and biofouling of MEMS drug delivery devices." *Biomaterials* 24 (11): 1959-1967.
16. Benoit, M., (2002) "Cell Adhesion Measured by Force Spectroscopy on Living Cells", *Methods in Cell Biology*, 68:91-114.
17. Wojcikiewicz, E., Zhang, X., and Moy, V., Force and Compliance Measurements on Living Cells Using Atomic Force Microscopy (AFM). *Biol. Proced. Online*, 2004. 6 (1): p. 1-9.

The disclosures of the cited patent documents, publications and/or references are incorporated herein in their entirety to the extent not inconsistent with the teachings herein.

While a number of embodiments of the present invention have been shown and described herein in the present context, such embodiments are provided by way of example only, and not of limitation. Numerous variations, changes and substitutions will occur to those of skill in the art without departing from the invention herein. For example, the present invention need not be limited to best mode disclosed herein, since other applications can equally benefit from the teachings of the present invention. Accordingly, it is intended that the invention be limited only by the spirit and scope of the appended claims in accordance with relevant law as to their interpretation.

What is claimed is:

1. A method of screening for biointeractive nanostructures comprising:
    providing a plurality of nanostructure candidates on a substrate; and
    interacting said nanostructure candidates with a SPM probe comprising a cantilever unit that comprises a lever portion and a probe portion provided at a free end of said lever portion, said probe portion comprising one or more living cells adhered thereto;
    wherein a nanostructure candidate exhibiting adhesion to said probe is identified as a biointeractive nanostructure.

2. The method of claim 1, wherein said one or more living cells comprises wherein nanostructure are provided via e-beam lithography.

3. The method of claim 1, further comprising:
    obtaining a first adhesion value of one or more of said plurality of nanostructure candidates utilizing a first SPM probe comprising one or more cells of a first cell-type adhered thereto;
    obtaining a second adhesion value of one or more of said plurality of nanostructure candidates utilizing a second SPM probe comprising one or more living cells of a second cell-type adhered thereto, and
    comparing said first and second adhesion values, wherein a nanostructure candidate having differential adhesion forces between first and second SPM probes is identified as a differentially adhesive nanostructure.

4. A system for identifying biointeractive nanostructures comprising
    a surface force microscope comprising a SPM probe associated therewith, said SPM probe comprising a cantilever unit that comprises a lever portion and a probe portion provided at a free end of said lever portion, said probe portion comprising one or more living cells adhered thereto, and a displacement detection system for detecting displacement of said probe; and
    a substrate associated with said surface force microscope, said substrate comprising a plurality nanostructures defined thereon.

5. The system of claim 4, wherein said plurality of nanostructures is defined on said substrate via ebeam lithography.

* * * * *